United States Patent [19]

Okada et al.

[11] Patent Number: 5,320,944
[45] Date of Patent: Jun. 14, 1994

[54] IMMUNOASSAY USING MAGNETIC PARTICLE

[75] Inventors: Masahisa Okada, Machida; Yoshihiro Ashihara, Fuchu; Akira Yano, Tokorozawa; Masao Oishi, Neyagawa; Katsuaki Yoshioka, Nerima; Toshiomi Nakamura, Yokohama, all of Japan

[73] Assignees: Fujirebio Inc., Tokyo; Nippon Paint Co., Ltd., Osaka, both of Japan

[21] Appl. No.: 965,612

[22] Filed: Oct. 22, 1992

Related U.S. Application Data

[63] Continuation of Ser. No. 590,834, Sep. 28, 1990, abandoned.

[30] Foreign Application Priority Data

Sep. 29, 1989 [JP] Japan .................................. 1-252051

[51] Int. Cl.$^5$ ........................................... G01N 33/535
[52] U.S. Cl. .................... 435/7.94; 436/526; 436/806; 435/968; 427/128; 427/130; 427/132; 427/217; 427/222
[58] Field of Search ............. 435/7.9, 7.91, 7.92, 435/7.94, 968; 436/526, 531, 806; 427/132, 304, 126.6, 217, 222, 128, 130, 212, 214

[56] References Cited

U.S. PATENT DOCUMENTS

| | | | |
|---|---|---|---|
| 4,177,253 | 12/1979 | Davies | 424/1 |
| 4,335,094 | 6/1982 | Mosbach | 424/1 |
| 4,672,040 | 6/1987 | Josephson | 436/526 |
| 4,978,614 | 12/1990 | Bronstein | 435/6 X |

FOREIGN PATENT DOCUMENTS

| | | | |
|---|---|---|---|
| 0149565 | 7/1985 | European Pat. Off. | G01N 33/53 |
| 0234083 | 9/1987 | European Pat. Off. | . |
| 8800695 | 1/1988 | European Pat. Off. | G01N 21/76 |
| 0259194 | 3/1988 | European Pat. Off. | . |
| 8904373 | 5/1989 | European Pat. Off. | C12Q 1/68 |

OTHER PUBLICATIONS

Oellerich, M., J. Clin. Chem. Clin. Biochem. vol. 22, pp. 895–904, (1984).

*Primary Examiner*—Esther L. Kepplinger
*Assistant Examiner*—Susan C. Wolski
*Attorney, Agent, or Firm*—Jordan and Hamburg

[57] ABSTRACT

An immunoassay method using magnetic particles comprising a core and a coating layer on the surface thereof, The core comprises an organic polymer and the coating layer comprises an iron oxide type ferrite coating layer. An antigen or an antibody is bound onto the surface of the coating layer and the particle has a particle size of 0.2 to 3 μm.

22 Claims, 1 Drawing Sheet

IMMUNOASSAY USING MAGNETIC PARTICLE

This is a continuation of application Ser. No. 07/590,834, filed Sep. 28, 1990, now abandoned.

FIELD OF THE INVENTION

This invention relates to an immunoassay using magnetic particles, more specifically to an enzyme immunoassay using magnetic particles in which a core comprises an organic polymer and a surface comprises a ferrite coating layer composed of iron oxide and an antigen or antibody is bound thereto, and a particle size of which is 0.2 to 3 μm.

BACKGROUND OF THE INVENTION

In an immunoassay, particularly in an enzyme immunoassay, it is advantageous to effect immuno reaction with high sensitivity since it employs in a solid phase latex particles with smaller particle sizes in place of beads having larger particle sizes. However, when particles having smaller particle sizes are employed, for effecting B/F separation, a centrifugal separator should be used or filtration by using a filter should be done. Thus, it cannot help saying that the method is simple. As a method for effecting B/F (Bound free) separation effectively and simply, there has been proposed a method in which magnetic particles having smaller particle size are employed. As such methods, there have been known that an immunoassay using particles having 1.0 to 10.0 μm wherein a silane is coated on magnetite as a core (see Japanese Provisional Patent Publications No. 141670/1980 and No. 122997/1975) and an immunoassay using particles having 0.1 to 1.5 μm wherein a silane is coated on a magnetic metal oxide as a core (see Japanese Provisional Patent Publication No. 1564/1985). In either of magnetic particles, the core comprises a magnetic metal and a silane is used for coating thereon.

Particles comprising these magnetic metals as a core have problems that they are insufficient in uniformity of particle size, and also poor in preservation stability for a long period of time since iron was dissolved out. Thus, in immunoassay methods using these particles, reproducibility of the measurement results is poor and preservation of a reagent used for the measurement could not be done for a long period of time.

SUMMARY OF THE INVENTION

The present inventors have studied intensively to overcome these problems and as the results, they have found that when magnetic particles which comprise a core composed of an organic polymer and a surface composed of an iron oxide type ferrite coating layer, with a particle size of 0.2 to 3 μm and an antigen or an antibody is bound on the particles are employed for an immunoassay method, measurement results excellent in reproducibility could be obtained. This can be also understood from the fact that said magnetic particles are stable for a long period of time so that preservation for a long period of time can be done.

DESCRIPTION OF THE PREFERRED EMBODIMENTS

Figure 1:
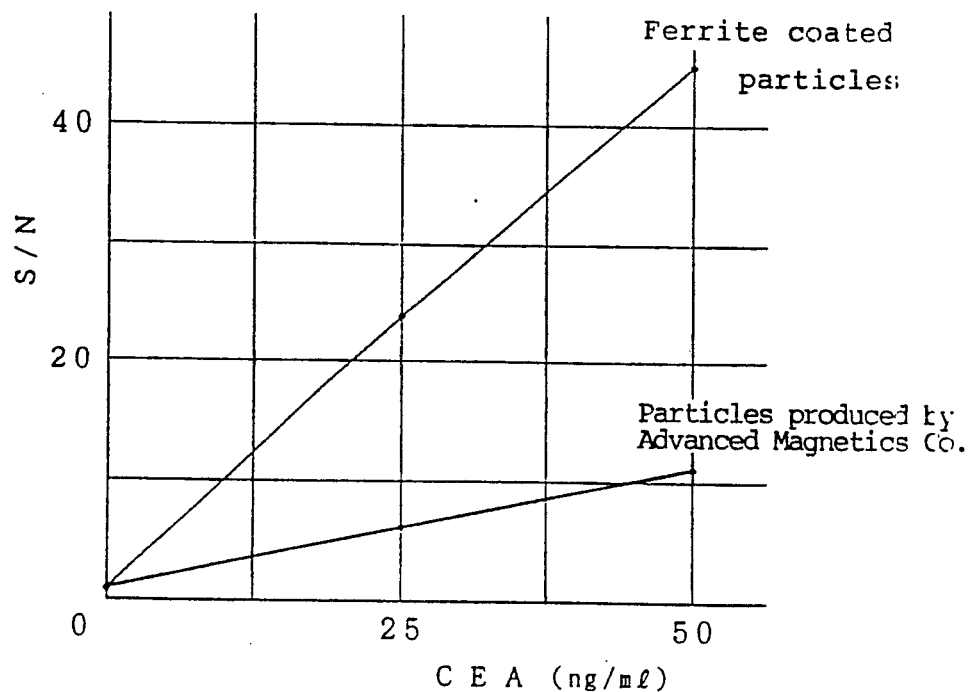
FIG. 1 is a graph showing results of CEA assay using ferrite coating particles and particles manufactured by Advanced Magnetics Co.

In the following, the present invention will be described in more detail.

Preparation of magnetic particles

The magnetic particles to be used in the present invention can be prepared by using an organic polymer as a core and subjecting to an iron oxide type ferrite coating, and then binding an a or an antibody to the resulting magnetic particles. The organic polymer comprises at least one polymer a polystyrene and or at least one of an acrylate and a methacrylate (hereinafter (meth)acrylates).

Examples of (meth)acrylates may include 2-hydroxyethyl (meth)acrylate, 2-hydroxypropyl (meth)acrylate, 1-methyl-2-hydroxyethyl (meth)acrylate, glycerol monomethacrylate, 2-acrylamido-2-methylpropane sulfonic acid, 2-sulfoethyl methacrylate, acid phosphoxyethyl methacrylate, 3-chloro-2-acid phosphoxypropyl methacrylate, acid phosphoxypropyl methacrylate, ethyl (meth)acrylate, n-butyl (meth)acrylate, i-butyl (meth)acrylate, 2-ethylhexyl (meth)acrylate, lauryl methacrylate, cyclohexyl methacrylate, (meth)acrylamide, N-methylol acrylamide, N-butoxymethyl acrylamide, glycidyl (meth)acrylate and methylglycidyl (meth)acrylate.

As the method of polymerization using these monomers, the emulsion polymerization and the multistage emulsion polymerization can be used. As the emulsion polymerization method, there has been known the method in which polymerization is carried out by charging whole monomer composition at one time, the monomer addition method in which a part of monomers and other components than the monomers are prepolymerized and then polymerization is further carried out by continuously adding the remaining monomers to the prepolymer, and the emulsion addition method in which polymer compositions are previously emulsified to effect prepolymerization of a part thereof, and then remaining emulsions are continuously added to proceed the polymerization. Also, the multistage polymerization method in which seed latex particles are stepwisely grown without generating new latex particles has been known.

For effecting these polymerization reactions, an organic peroxide type initiator such as benzoyl peroxide, lauroyl peroxide, cumen hydroperoxide, di-t-butylperoxide and acetyl peroxide and a nitrile type initiator such as α,α'-azobisisobutyronitrile have been known as a radical polymerization initiator.

Also, a compound which utilizes pyrolysis, such as potassium persulfate, ammonium persulfate and hydrogen peroxide may be used. Further, a redox type polymerization catalyst may be employed. As an emulsifier to be used for the emulsion polymerization, there may be mentioned an ionic active agent such as an anionic active agent, cationic active agent, amphoteric active agent and nonionic active agent.

Next, ferrite coating is carried out to the core of organic polymer obtained by the method as mentioned above to form ferrite coated particles.

The ferrite coating is carried out in an aqueous solution containing core particles. The aqueous solution contains ferrous ions which are essential for forming ferrite coatings. The ferrous ions are supplied in the aqueous solution in the form of a ferrous salt such as hydrochloride, sulfate and acetate. When the aqueous solution contains only ferrous ions as the metal ion, the coating can be obtained as a spinel ferrite which contains only iron as a metal element, i.e. coatings of magnetite $Fe_3O_4$. Also, in the aqueous solution, other transition metal ion $M^{n+}$ may be contained in addition to the ferrous ion. Such other metal ion species may include zinc, cobalt, nickel, manganese, copper, vanadium, antimony, lithium, molybdenum, titanium, rubidium, aluminum, silicon, chromium, tin, calcium, cadmium and indium. When the $M^{n+}$ is cobalt, coatings of cobalt ferrite ($Co_xFe_{3-x}O_4$) and nickel ferrite ($Ni_xFe_{3-x}O_4$) can be obtained, and when the $M^{n+}$ is plural kinds of species, mixed crystal ferrite can be obtained. These metal ion species other than ferrous ion can be formulated in the aqueous solution in the form of salts.

In the present invention, formation of ferrite coatings is started by adding an oxidizing agent solution to a dehydrogenated aqueous solution containing ferrous ions and core particles. Examples of the oxidizing agent may include nitrites, nitrates, hydrogen peroxide, organic peroxides, perchlorates and oxygen-dissolved water. More preferably, an aqueous solution of the oxidizing agent is added dropwise in the solution with a constant ratio as in the titration method of analytical chemistry. According to the dropwise addition with a content ratio, a thickness of the ferrite coatings can be easily adjusted.

A pH of the aqueous solution can be optionally selected depending on the kinds of anions and metal ions present in an aqueous solution and can be controlled, but preferably in the range of 6 to 11, more preferably 7 to 11. For stabilizing the pH, a buffer such as ammonium acetate or a salt having a buffering effect may be added.

A temperature to carry out the reaction of the present invention may be in the range of the boiling point of the aqueous solution or lower, but the reaction is preferably carried out in the range of 60° C. to 90° C. Also, the reaction is carried out under a substantially deoxidized atmosphere. Under the conditions existing a large amount of oxygen, an oxidization reaction proceeds unnecessarily. More specifically, it is preferred to carry out the reaction under nitrogen atmosphere. Also, oxygen is removed from the aqueous solution to use a deoxidized aqueous solution, similarly.

A suitable method in the present invention is firstly to suspend particulate materials in the deoxidized water. At this time, wetting of the particulate materials to water may be improved by, if necessary, adding an additive such as a surfactant. Then, if necessary, a pH buffer, etc. may be added to adjust a pH, and then ferrous ions are added thereto in the form of a salt. Also, other metal ions may be added thereto simultaneously with the ferrous ions depending on necessity. After completion of addition of whole components, the reaction is initiated by adding an oxidizing agent solution to the mixture solution with the titration method as mentioned above. This procedure is particularly preferred since the thickness of the ferrite coatings can be controlled by the concentration of the metal ion species or the oxidizing agent. The resulting particulate materials subjected to ferrite coatings are separated by filtration and dried to obtain the desired products.

Preparation of particles treated by polymer compound

The magnetic particles to be used in the present invention may be used after treating with a polymer compound. As the polymer compound, there may be used, for example, a silane, nylon (trade name) or a polystyrene. As the method of silane treatment, for example, the acidic aqueous silylation method may be used. It can be accomplished by, firstly mixing ferrite coated particles and silane monomer in an acidic solution, and then treating the mixture at room temperature to 95 C under heating. As the silane monomer to be used, there may be used, for example, an aminopropyltrimethoxysilane, N-2-aminoethyl-3-aminopropyltrimethoxysilane, triamino-functional silane ($H_2NCH_2CH_2NHCH_2CH_2$-$NHCH_2CH_2CH_2$-$Si$-$(OCH_3)_3$), n-dodecyltriethoxysilane and n-hexyltrimethoxysilane. Further, in order to convert an end amino group of the silane into carboxylic group, an acid anhydride can be reacted to silane-treated particles at room temperature. Also, for treating polyamide, ferrite coated particles are suspended in a 1% aqueous sodium carbonate solution, dissolving an appropriate amount of hexamethylenediamine therein, and mixing 5-fold amounts of a hexane-chloroform mixed solution (3 : 1) containing 8% Tween 80 (trade name,) to the solution, and then subjecting to ultrasonic treatment to form an emulsion. Then, by adding dropwise the same hexane-chloroform mixed solution as mentioned above containing sebacoyl dichloride with an equimolar amount to hexamethylenediamine, the desired particles can be obtained. Also, in the case of a polystyrene, it can be treated by employing the method known in the art. Further, magnetic particles can be directly coated by spraying or dipping in a polymer resin solution such as nylon (trade name) and a polystyrene.

The present invention relates to magnetic particles obtained by binding an antigen or an antibody to the ferrite coated particles or further polymer compound-treated particles obtained by the above method. As the antibody to be used, there may be mentioned, for example, a chemical such as theophylline, phenytoin and a low molecular hormone such as thyroxine, estrogen and estradiol; a cancer marker such as CEA and AFP; a virus antigen such as HIV, ATLA and HBV; a high molecular hormone such as TSH and insulin; a cytocain such as IL-1, IL-2 and IL-6; various kinds of gloss factor such as EGF and PDGF; and further an antibody to a suitable DNA, RNA, etc. of the above viruses. Also, as the antigen to be used, there may be mentioned a virus such as HIV, ATLA and HBV; DNA of the above viruses; a high molecular hormone such as insulin and TSH.

As the bonding method, the physical absorption method or the chemical bonding method may be employed. The physical absorption method is carried out in an appropriate buffer solution by reacting the above particles and an antigen or an antibody. As the buffer solution to be used in this reaction, there may be mentioned a phosphate buffer solution, a tris-hydrochloride buffer solution and a carbonate buffer solution. The reaction can proceed easily by mixing both of the components at room temperature to obtain the desired product. Also, as the chemical bonding method, the carbodiimide method in the so-called peptide bonding method can be employed. Bonding can be carried out, for example, by adding an equiamount of a water-soluble carbodiimide to a dispersion of 0.1 to 5% of silylated particles under acidic conditions (pH 4 to 6), reacting at room temperature for 10 minutes to one hour, removing a supernatant, and then adding 0.01 to 10.0 mg/ml, preferably 0.1 to 5 mg/ml of an antibody or an antigen solution. The buffer to be used at this time is preferably a phosphate buffer. Also, as the other chemical bonding method, the method in which the reaction is carried out in the presence of a divalent cross-linking reagent such as glutaraldehyde and cyanuric chloride may be employed (see "Peptide Synthetic Method", published by Maruzene K.K. (published in 1975) and "Enzyme Immunoassay Method", published by Kyoritsu Shuppan K.K., "Protein, Nucleic acid, Enzyme", special issue No. 31 (1987)).

The magnetic particles produced as mentioned above had a constant particle size. These particles had not changed even when they were preserved in an appropriate protein solution such as BSA and globulin for one year.

The magnetic particles according to the present invention have a particle size of 0.2 $\mu$m or more to 3 $\mu$m or less. If the particle size becomes in excess of 3 $\mu$m, floating time is short when they are used in immuno reaction so that sufficient reaction cannot be carried out. Also, if it is less than 0.2 $\mu$m, magnetic separating efficiency after immunoassay becomes bad.

Immunoassay method

As the immunoassay method in accordance with the present invention, the radioactive immunoassay method and the enzyme immunoassay method can be used. These assay methods are the immunoassay methods using a label and an antigen or an antibody to be assayed can be assayed by the sandwich method or the competition method.

The enzyme immunoassay method according to the present invention is, for example, to carry out by reacting an antibody-bound magnetic particle and an enzyme-labelled antibody for 10 minutes to 3 hours. A reaction temperature when practicing the reaction is 4° C. to 40° C., and preferably 25° C. to 38° C. After washing an unreacted enzyme-labeled antibody, an amount of a ligand of specimen can be determined by measuring an amount of an antigenbound enzyme bound to a solid phase, by adding an enzyme substrate and measuring an activity thereof. An enzyme to be used in the of the invention may include peroxidase, alkaline phosphatase, $\beta$-galactosidase and glucoseoxidase. At this time, it is needless to say that a substrate to be used should be that which is suitable for an enzyme to be used. As such substrates, there may be used, for example, ABTS, luminol-H2O2 (for peroxidase), 3-(2'-pyro-tricyclo[3.3.1.1$^{3,7}$]decan)-4-methoxy-4(3''-phosphoryloxy) phenyl-1,2-dioxetane disodium salt, p-nitrophenylphosphate and methylumbelliferyl phosphate (for alkaline phosphatase), p-nitrophenyl-$\beta$-o-glactose and methylumbelliferyl-$\beta$-o-galactose (for $\beta$-galactosidase). The measurement can be carried out by reacting at room temperature to 40° C. for 1 minute to 18 hours, and then measuring an amount of color, fluorescence or luminescence generated. As the other method, the so-called rate method in which it is carried out at a temperature range of 4° C. to 40° C. under heating may be employed.

Also, the radioimmunoassay method in the immunoassay method is carried out by labelling a radioisotope such as $^{125}$I in place of the above enzyme label. Operations are quitely the same with the above enzyme immunoassay method except for measuring radioactivity.

Also, radiolabelling of an antigen or an antibody can be readily prepared by the already available Bolton-Hunter reagent. It can be prepared by, for example, adding the Bolton-Hunter reagent to an antigen or an antibody solution dissolved in a 0.1 M sodium hydrogen carbonate aqueous solution, and after 1 to 2 hours, removing unreacted Bolton-Hunter reagent by using a desalting column of G-25, etc. In addition, radiolabelling of 125I can be easily carried out by employing the chloramine T method or the iodine method. For effecting the immuno reaction, a sample is added to the magnetic particles of the present invention, and reacted at 4° C. to 40° C., preferably 20° C. to 38° C. for 1 to 18 hours. Thereafter, washing is carried out by a physiological salt solution or distilled water, radiolabelled antibody is added to magnetic particles and reacted at 4° C. to 40° C., preferably 20° C. to 38° C. for 1 to 18 hours, washed with a physiological salt solution or distilled water and then countering its radioactivity. A scintillation counter can be used for the measurement.

Also, the assay method of the present invention may be carried out by the chemiluminescent assay method in which isoluminol or acridine ester is labelled, or the fluorescent immunoassay method in which fluoresceine or rhodamine is labelled. During the procedures, labelling of a labelling substance can be easily carried out by employing the active ester method or the isocyanate method (see "Enzyme immunoassay method" (published by Igaku Shoin, 1987)).

Similarly, measurement of the antibody can be carried out by using the magnetic particles of the present invention, mixing these particles with a sample to react them at a room temperature to 37° C. for one minute to 18 hours, washing with a physiological salt solution or distilled water, and then adding labelled-anti-human immunoglobulin antibody to react at a room temperature to 37° C. for 1 minute to 18 hours, washing and measuring the activity of the labelled substance.

The present invention is an enzyme immunoassay method using particles comprising magnetic particles composed of an organic polymer as a core and a ferrite layer deposited on the surface thereof, and an antigen or antibody bound on the surface of the ferrite layer. These particles may be used as a solid phase of an immunoassay method.

EXAMPLES

In the following, the present invention will be explained by referring to Examples in more detail.

EXAMPLE 1

Preparation of organic polymer particles

In an apparatus for polymerization reaction having a stirrer, a thermometer, a monomer-dropping funnel, a reflux condenser, a heating device and a nitrogen gas inlet tube was charged 230 parts of deionized water, followed by adding 1 part of a mixed monomer (A) composed of styrene, 2-ethylhexyl acrylate and ethyleneglycol dimethacrylate (80/10/10) and 10 parts of a 10% aqueous ammonium persulfate solution, and then adding dropwise 99 parts of the above mixed monomer (A) over 3 hours to obtain a latex. When the particles were observed by electron microscope, they were substantially monodispersed and a particle size of 0.3 $\mu$m.

Preparation of ferrite coated particles

In a magnetic particle preparing apparatus having a stirrer, a thermometer, an oxidizing agent dropping funnel, a heating device and a nitrogen gas inlet tube was charged 100 parts of the above emulsion (30% solid content) and degassed oxygen in the core emulsion by introducing $N_2$ gas.

Then, previously prepared 100 parts (solid content: 40 parts) of ferrous chloride solution and 150 parts (solid content: 75 parts ) of ammonium acetate were thrown in the apparatus and the mixture was sufficiently stirred at 70° C. under heating. Thereafter, while continuing stirring, a pH of the mixture was adjusted to 7.2 with aqueous ammonia.

To the solution was added dropwise 150 parts (solid content: 15 parts) of a sodium nitrite solution over about one hour. During dropwise addition and reaction, a temperature of the mixture was maintained to 70° C. and a pH in the range of 7.0 to 7.2 while continuing introduction of nitrogen gas and stirring to form ferrite coatings on the surfaces of said particles. After about 20 minutes, the solution was cooled, and repeated to filtering and washing with deionized water, and then taken out particles to obtain ferrite coated particles.

EXAMPLE 2

Preparation of anti-TSH mouse IgG-bound magnetic particles

To 4 ml of a 5% ferrite coated particles-dispersed aqueous dispersion (20 mM phosphate buffer, pH 3.5) prepared in Example 1 was added 1 ml of anti-TSH mouse IgG (5 mg/ml), and the mixture was stirred by an end-over-end mixer at room temperature overnight. After separating this particle dispersion with a magnet having 3000 gauss at the surface thereof to a supernatant and particles, the supernatant was removed, and the particles were washed five times with a 2 % BSA solution (0.1 M Tris-hydrochloric acid, 1 mM magnesium chloride and 0.1 mM zinc chloride, pH: 7.5). Then, the particles were dispersed in 5 ml of the similar BSA solution to prepare magnetic particles.

EXAMPLE 3

Preparation of anti-CEA mouse IgG-bound magnetic particles

To 4 ml of a 5% ferrite coated particles-dispersed aqueous dispersion (20 mM phosphate buffer, pH 3.5) prepared in Example 1 was added 1 ml of anti-CEA mouse IgG (5 mg/ml), and the mixture was stirred by an end-over-end mixer at room temperature overnight. After separating this particle dispersion with a magnet having 3000 gauss at the surface thereof to a supernatant and particles, the supernatant was removed, and the particles were washed five times with a 2% BSA solution (0.1 M Tris-hydrochloric acid, 1 mM magnesium chloride and 0.1 mM zinc chloride, pH: 7.5). Then, the particles were dispersed in 5 ml of the similar BSA solution to prepare magnetic particles.

EXAMPLE 4

Preparation of carboxylated-ferrite particles

Carboxylated ferrite particles can be obtained by adding 50 ml of 3-aminopropyltriethoxysilane to 5 g of ferrite particles (polystyrene having an average particle size of the core of 0.3 μm) of Example 1 which had been previously washed 5 times for each 60 seconds with distilled water by using an ultrasonic washing machine (Batt type, manufactured by Nippon Seiki Seisakusho K.K.), further adding 30 ml of glacial acetic acid to react at room temperature for 3 hours, followed by washing and reacting with glutaric acid anhydride. Glacial acetic acid was added dropwise under ice-cooling and stirring, and washing was carried out each three times with distilled water, methanol and distilled water, and further five times with each 300 ml of 0.1M sodium hydrogen carbonate solution. The reaction with glutaric acid was carried out by adding 2.85 g of glutaric acid anhydride to 100 ml of 5% by weight (0.1 M sodium hydrogen carbonate solution) particles and reacting for 10 minutes. After completion of the reaction, the mixture was washed three times with each 300 ml of 0.1 M sodium hydrogen carbonate solution, and further five times with distilled water. This was used as carboxylated ferrite particles.

EXAMPLE 5

Preparation of anti-TSH bound carboxylated-ferrite

In 5 ml of 20 mM phosphate buffer (pH 4.5) was dispersed 50 mg of carboxylated ferrite particles prepared in Example 4, followed by adding 50 mg of water-soluble carbodiimide. After reacting at room temperature for 20 minutes, the supernatant was removed, and 5 ml of anti-TSH mouse IgG solution (1 mg/ml, 0.02 M phosphate buffer solution, pH: 4.5), and the mixture was stirred by an end-over-end mixer. After 2 hours, these particles were washed five times with 2% BSA solution (0.1 M Tris-HCl, 1 mM $MgCl_2$, pH: 7.5) and dispersed in the similar BSA solution to obtain anti-TSH-mouse IgG sensitized carboxylated-ferrite particles.

EXAMPLE 6

TSH assay using anti-TSH sensitized ferrite particles

To a sample containing 15 μl of TSH (0, 10 μU/ml) was mixed 20 μl of alkali phosphatase conjugate (conjugate concentration: 0.5 μg/ml, 0.1 M Tris-hydrochloric acid, 2% BSA, 1 mM $MgCl_2$, 0.1 mM $ZnCl_2$, pH: 7.5) to which anti-TSH Fab' is bound, and then 500 μl (0.02% solution) of ferrite particles prepared in Example 2 on which anti-TSH mouse IgG was coated was mixed to the above mixture, and the resulting mixture was allowed to stand at room temperature for 20 minutes. A tube containing the above mixture was contacted with a magnet having a surface magnetic field of 3000 gauss to attract ferrite particles and the supernatant was removed by decantation. Thereafter, 1 ml of 0.04% physiological salt solution was added to the particles and the mixture was stirred. The tube was again contacted with the above mentioned magnet to separate the particles and a supernatant, and the supernatant was removed by decantation. These operations were repeated three times. To the tube containing these particles was added 200 μl of a substrate solution (0.1 M Tris-hydrochloric acid, 1 μM MgCl2, 0.1 mM ZnCl2, pH: 9.8) containing 100 μg/ml of 3-(2'-pyro-tricyclo[3.3 1.1$^{3,7}$]decan)-4-(3''-phosphoryloxy) phenyl-1,2-dioxetane disodium salt (AMPPD) and the mixture was reacted at room temperature. After carrying out the reaction for 17 minutes, the sample was measured by a luminometer (manufactured by Belthold Co.). In Table 1, an S/N ratio of integrated value for 5 minutes was shown. For comparison, the results wherein ferrite particles produced by Advanced Magnetics Co. [magnetic carrier for Affinity Chromatography (carboxyl group terminated)] were used are also shown.

TABLE 1

|  | S/N ratio | Magnification |
| --- | --- | --- |
| Ferrite coated particles | 47.4 | 6.2 |

TABLE 1-continued

| | S/N ratio | Magnification |
|---|---|---|
| Particles produced by Advanced Magnetics Inc. | 7.6 | 1 |

EXAMPLE 7

TSH assay using carboxylated particles

To a sample containing 15 μl of TSH (0, 10 μU/ml) was mixed 20 μl of alkali phosphatase conjugate (conjugate concentration: 0.5 μg/ml, 0.1 M Tris-hydrochloric acid, 2% BSA, 1 mM $MgCl_2$, 0.1 mM $ZnCl_2$, pH: 7.5) to which anti-TSH Fab' is bound, and then 500 μl (0.02% solution) of carboxylated ferrite particles prepared in Example 5 on which anti-TSH mouse IgG was coated was mixed to the above mixture, and the resulting mixture was allowed to stand at room temperature for 20 minutes. A tube containing the above mixture was contacted with a magnet having a surface magnetic field of 3000 gauss to attract ferrite particles and the supernatant was removed by decantation. Thereafter, 1 ml of 0.04% physiological salt solution was added to the particles and the mixture was stirred. The tube was again contacted with the above mentioned magnet to separate the particles and a supernatant, and the supernatant was removed by decantation. These operations were repeated three times. To the tube containing these particles was added 200 μl of a substrate solution (0.1 M Tris-hydrochloric acid, 1 μM MgCl2, 0.1 mM ZnCl2, pH: 9.8) containing 100 μg/ml of AMPPD and the mixture was reacted at room temperature. After carrying out the reaction for 17 minutes, the sample was measured by a luminometer (manufactured by Belthold Co.).

In Table 2, an S/N ratio of integrated value for 5 minutes was shown. For comparison, the results wherein ferrite particles produced by Advanced Magnetics Inc. [magnetic carrier for Affinity Chromatography (carboxyl group terminated)] were used are also shown.

TABLE 2

| | S/N ratio | Magnification |
|---|---|---|
| Ferrite coated particles | 78.2 | 10.0 |
| Particles produced by Advanced Magnetics Inc. | 7.6 | 1 |

EXAMPLE 8

CEA assay using anti-CEA sensitized ferrite particles

To a sample containing 15 μl of CEA (0, 25, 50 ng/ml) was mixed 20 μl of alkali phosphatase conjugate (conjugate concentration: 0.2 μg/ml, 0.1 M Tris-hydrochloric acid, 2% BSA, 1 mM MgCl2, 0.1 mM ZnCl2, pH: 7.5) to which anti-CEA Fab' is bound, and then 500 μl (0.02% solution) of ferrite particles prepared in Example 3 on which anti-CEA mouse IgG was coated was mixed to the above mixture, and the resulting mixture was allowed to stand at room temperature for 20 minutes. A tube containing the above mixture was contacted with a magnet having a surface magnetic field of 3000 gauss to attract ferrite particles and the supernatant was removed by decantation. Thereafter, 1 ml of 0.04% physiological salt solution was added to the particles and the mixture was stirred. The tube was again contacted with the above mentioned magnet to separate the particles and a supernatant, and the supernatant was removed by decantation. These operations were repeated three times. To the tube containing these particles was added 200 μl of a substrate solution (0.1 M Tris-hydrochloric acid, 1 μM MgCl2, 0.1 mM ZnCl2, pH: 9.8) containing 100 μg/ml of AMPPD and the mixture was reacted at room temperature. After carrying out the reaction for 17 minutes, the sample was measured by a luminometer (manufactured by Belthold Co.).

In FIG. 1, an S/N ratio of integrated value for 5 minutes was shown. For comparison, the results wherein ferrite particles produced by Advanced Magnetics Inc. [magnetic carrier for Affinity Chromatography (carboxyl group terminated)] were used are also shown.

EXAMPLE 9

Comparison of magnetic separating rate of ferrite particles

In a tube was charged 500 μl of 0.02% anti-TSH mouse IgG bound ferrite particles (2% BSA, 0.1 M Tris-HCl, 1 mM MgCl2, pH: 9.8), and the tube was contacted with a magnet having a surface magnetic field of 3000 gauss.

Figure 2:
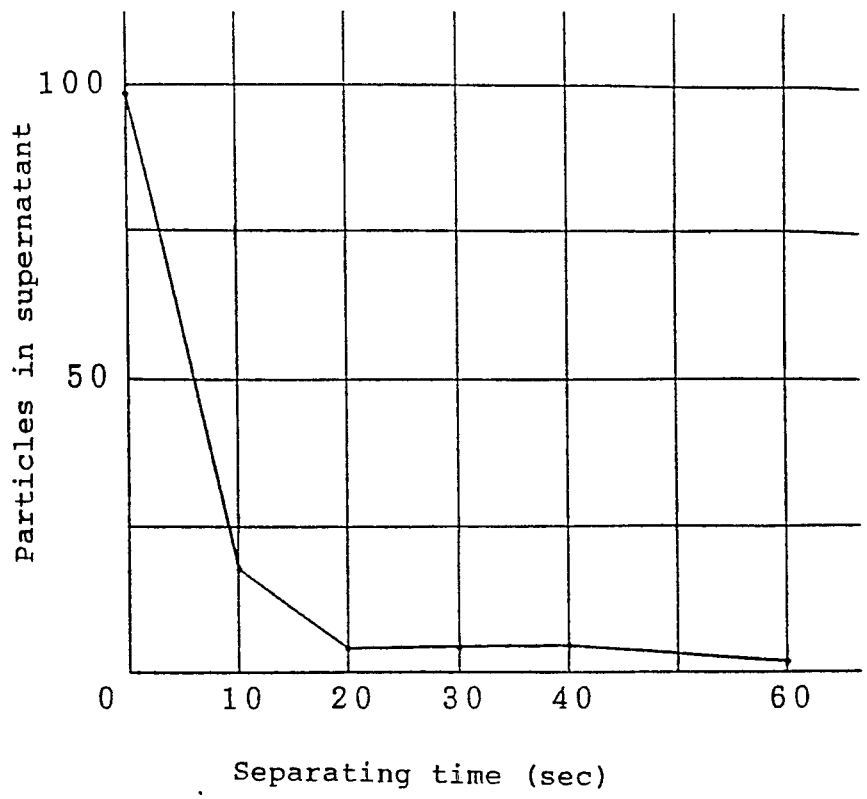
FIG. 2 is a graph showing magnetic particles separating rate of ferrite particles.

After 0, 10, 20, 30, 40 and 60 seconds of the contact, a supernatant was separated and an absorption at a wavelength of 660 nm was measured. The results of separating rate were shown in FIG. 2.

EXAMPLE 10

Investigation of floating property of particles

Anti-TSH mouse IgG bound ferrite particles (0.02%) was charged in a 1000 μl tube and allowed to stand at room temperature.

Supernatants at 0 minute and after 30 minutes were sampled and absorption at a wavelength of 660 nm was measured. Its relative turbidity was shown in Table 3.

TABLE 3

| | Relative turbidity |
|---|---|
| Ferrite coated particles | 80% |
| Particles produced by Advanced Magnetics Inc. | 72% |

(The relative turbidity means a turbidity after "30 minutes" when a turbidity at "0 minute after allowed to stand" as "100%".)

The present invention relates to an enzyme immunoassay method using particles composed of a magnetic particle comprising an organic polymer as a core and a ferrite coatings coated on the surface thereof, and an antigen or antibody bound to the surface of the magnetic particle. The particles according to the present invention have uniform particle size and are excellent in binding state of an antigen or antibody to the particles. Further, the particles according to the present invention have advantages that they are stable for a long period of time and thus can be preserved. An enzyme immunoassay method according to the present invention can be carried out by using the particles rapidly and with high sensitivity.

What is claimed is:

1. An immunoassay method comprising the steps of:
    (a) reacting a sample containing an antigen with an antibody which specifically binds to said antigen, so as to bind said antigen to said antibody, wherein said antibody is immobilized on a 0.2 to 3.0 μm magnetic particle comprising a core and a coating layer on the surface of said core, wherein said core comprises an organic polymer and said coating layer comprises a metal oxide formed by adding ferrous ions or ferrous ions and an ion selected from the group consisting of zinc, cobalt, nickel, manganese, copper, vanadium, antimony, lithium, molybdenum, titanium, rubidium, aluminum, silicon, chromium, tin, calcium, cadmium, indium ions and mixtures thereof to deoxidized water in which cores of organic polymer are suspended to form a resulting solution, and subsequently adding an oxidizing agent solution to the resulting solution to provide a ferrite coating on said core;

(b) measuring an amount of bound antigen; and
(c) correlating the amount of bound antigen obtained in step (b) with an amount of antigen in the sample.

2. An immunoassay method comprising the steps of:
(a) reacting a sample containing an antibody with an antigen which specifically binds to said antibody, so as to bind said antibody to said antigen, wherein said antigen is immobilized on a 0.2 to 3.0 μm magnetic particle comprising a core and a coating layer on the surface of said core, wherein said core comprises an organic polymer and said coating layer comprises a metal oxide formed by adding ferrous ions or ferrous ions and an ion selected from the group consisting of zinc, cobalt, nickel, manganese, copper, vanadium, antimony, lithium, molybdenum, titanium, rubidium, aluminum, silicon, chromium, tin, calcium, cadmium, indium ions and mixtures thereof to deoxidized water in which cores of organic polymer are suspended to form a resulting solution, and subsequently adding an oxidizing agent solution to the resulting solution to provide a ferrite coating on said core;

(b) measuring an amount of bound antibody; and
(c) correlating the amount of bound antibody obtained in step (b) with an amount of antibody in the sample.

3. An immunoassay method according to claim 1, wherein said method is an enzyme immunoassay method.

4. An immunoassay method according to claim 2, wherein said method is an enzyme immunoassay method.

5. An immunoassay method according to claim 1, wherein said particle is further coated with a polymer selected from the group consisting of silane, nylon and polystyrene prior to immobilization of the antibody.

6. An immunoassay method according to claim 2, wherein said particle is further coated with a polymer selected from the group consisting of silane, nylon and polystyrene prior to immobilization of the antigen.

7. The immunoassay method according to claim 1, wherein said organic polymer of the core comprises an polystyrene or a polymer comprising at least one of an acrylate and a methacrylate.

8. The immunoassay method according to claim 2, wherein said organic polymer of the core comprises an polystyrene or a polymer comprising at least one of an acrylate and a methacrylate.

9. The immunoassay method according to claim 1, wherein said coating layer is a magnetite layer or a mixed crystal ferrite layer.

10. The immunoassay method according to claim 2, wherein said coating layer is a magnetite layer or a mixed crystal ferrite layer.

11. The immunoassay method according to claim 5, wherein (a) said sample comprises said antigen; (b) said antibody is immobilized on said magnetic particle; and (c) said method further comprises adding an enzyme-labeled antibody, which specifically binds to said antigen to the sample; and separating unreacted enzyme labeled antibody from the sample by washing out said unreacted enzyme-labeled antibody, adding an enzyme substrate specific for the enzyme and measuring the activity of antibody-bound enzyme.

12. The immunoassay method according to claim 6, wherein (a) said sample comprises said antigen; (b) said antibody is immobilized on said magnetic particle; and (c) said method further comprises adding an enzyme-labeled antigen, which specifically binds to said antibody to the sample; and separating unreacted enzyme-labeled antigen from the sample by washing out said unreacted enzyme-labeled antigen, adding an enzyme substrate specific for the enzyme and measuring the activity of antigen-bound enzyme.

13. The immunoassay method according to claim 11, wherein said enzyme substrate is selected from the group consisting of (i) ABTS and luminol-$H_2O_2$ for peroxidase; (ii) (2'-pyro-tri-cyclodecab)-4-(3''-phosphoryloxy)-phenyl-1,2-dioxetane disodium salt, p-nitrophenylphosphate and methylumbelliferyl phosphate for alkaline phosphatase; and (iii) p-nitrophenyl-β-o-galactose and methylumbelliferyl-β-o-galactose for β-galactosidase.

14. The immunoassay method according to claim 12, wherein said enzyme substrate is selected from the group consisting of (i) ABTS and luminol-$H_2O_2$ for peroxidase; (ii) (2'-pyro-tri-cyclodecab)-4-(3''-phosphoryloxy)-phenyl-1,2-dioxetane disodium salt, p-nitrophenylphosphate and methylumbelliferyl phosphate for alkaline phosphatase; and (iii) p-nitrophenyl-β-o-galactose and methylumbelliferyl-β-o-galactose for β-galactosidase.

15. The immunoassay method according to claim 13, wherein said enzyme substrate is (2'-pyro-tricyclo[3.3.1.1$^{3,7}$]-decan)-4-methoxy-4-(3''-phosphoryloxy) phenyl-1,2-dioxetane disodium salt.

16. The immunoassay method according to claim 14, wherein said enzyme substrate is (2'-pyro-tricyclo[3.3.1.1$^{3,7}$]-decan)-4-methoxy-4-(3''-phosphoryloxy) phenyl-1,2-dioxetane disodium salt.

17. The immunoassay method according to claim 3, wherein (a) said sample comprises said antigen; (b) said antibody is immobilized on said magnetic particle; and (c) said method further comprises adding an enzyme-labeled antigen, which specifically binds to said antibody to the sample; and separating unreacted enzyme labeled antigen from the sample by washing out said unreacted enzyme-labeled antigen, adding an enzyme substrate specific for the enzyme and measuring the activity of antigen-bound enzyme.

18. The immunoassay method according to claim 4, wherein (a) said sample comprises said antibody; (b) said antigen is immobilized on said magnetic particle; and (c) said method further comprises adding an enzyme-labeled antibody, which specifically binds to said antibody to the sample; and separating unreacted enzymelabeled antibody from the sample by washing out said unreacted enzyme-labeled antibody, and adding an enzyme substrate specific for the enzyme and measuring the activity of antibody-bound enzyme.

19. The immunoassay method according to claim 17, wherein said enzyme substrate is selected from the group consisting of (i) ABTS and luminol-$H_2O_2$ for peroxidase; (ii) (2'-pyro-tricyclo[$3.3.1.1^{3,7}$]decan)-4-methoxy-4-(3''-phosphoryloxy)-phenyl-1,2-dioxetane disodium salt, p-nitrophenylphosphate and methylumbelliferyl phosphate for alkaline phosphatase; and (iii) p-nitrophenyl-$\beta$-o-galactose and methylumbelliferyl-$\beta$-o-galactose for $\beta$-galactosidase.

20. The immunoassay method according to claim 18, wherein said enzyme substrate is selected from the group consisting of (i) ABTS and luminol-$H_2O_2$ for peroxidase; (ii) (2'-pyro-tricyclo[$3.3.1.1^{3,7}$]-decan)-4-methoxy-4-(3''-phosphoryloxy)-phenyl-1,2-dioxetane disodium salt, p-nitrophenylphosphate, and methylumbelliferyl phosphate for alkaline phosphatase; and (iii) p-nitrophenyl-$\beta$-o-galactose and methylumbelliferyl-$\beta$-o-galactose for $\beta$-galactosidase.

21. The immunoassay method according to claim 19, wherein said enzyme substrate is 2'-pyro-tricyclo[$3.3.1.1^{3,7}$]-decan)-4-methoxy-4-(3''-phosphoryloxy) phenyl-1,2-dioxetane disodium salt.

22. The immunoassay method according to claim 20, wherein said enzyme substrate is 2'-pyro-tricyclo[$3.3.1.1^{3,7}$]-decan)-4-methoxy-4-(3''-phosphoryloxy) phenyl-1,2-dioxetane disodium salt.

* * * * *